(12) United States Patent
Alferness et al.

(10) Patent No.: US 6,567,699 B2
(45) Date of Patent: May 20, 2003

(54) DEFIBRILLATING CARDIAC CONSTRAINT

(75) Inventors: Clifton A. Alferness, Redmond, WA (US); James Edward Shapland, Vadnais Heights, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 0 days.

(21) Appl. No.: 10/060,655

(22) Filed: Jan. 30, 2002

(65) Prior Publication Data

US 2002/0103511 A1 Aug. 1, 2002

Related U.S. Application Data

(63) Continuation of application No. 09/628,706, filed on Jul. 31, 2000, now Pat. No. 6,370,429, which is a continuation of application No. 09/195,770, filed on Nov. 18, 1998, now Pat. No. 6,169,922.

(51) Int. Cl.$^7$ .............................. A61N 1/39; A61N 1/36
(52) U.S. Cl. ............................... 607/5; 600/16; 600/37; 607/129; 607/2
(58) Field of Search ................................. 607/3, 5, 119, 607/122, 129; 600/16, 37; 623/3

(56) References Cited

U.S. PATENT DOCUMENTS

| | | | |
|---|---|---|---|
| 3,587,567 A | 6/1971 | Schiff | 601/21 |
| 3,983,863 A | 10/1976 | Janke et al. | 600/37 |
| 4,048,990 A | 9/1977 | Goetz | 601/153 |
| 4,403,604 A | 9/1983 | Wilkinson et al. | 600/37 |
| 4,428,375 A | 1/1984 | Ellman | 606/151 |
| 4,630,597 A | 12/1986 | Kantrowitz et al. | 600/18 |
| 4,690,134 A | 9/1987 | Snyders | 601/153 |

(List continued on next page.)

FOREIGN PATENT DOCUMENTS

| | | | |
|---|---|---|---|
| DE | 295 17 393 U1 | 3/1996 | |
| EP | 0 280 564 | 8/1988 | |
| EP | 0 303 719 | 2/1989 | |
| JP | 60203250 | 10/1985 | |
| JP | 01-145066 | 6/1989 | |
| SU | 1009457 A | 4/1983 | |
| WO | WO 98/29041 | 7/1998 | |
| WO | WO 98/58598 | 12/1998 | |
| WO | WO 99/52470 | * 10/1999 | A61F/2/04 |

OTHER PUBLICATIONS

Capouya, et al., "Girdling Effect of Nonstimulated Cardiomayoplasty on Left Ventricular Function," The Society of Thoracic Surgeons, 56:867–871 (1993).

Cohn, "The Management of Chronic Heat Failure", The New Eng. J. of Med., 335 (7): 490–498 (Aug. 15, 1996).

Kass et al., "Reverse Remodeling From Cardiomyoplasty in Human Heart Failure, External Constraint Versus Active Assist", Circulation 91 (9): 2314–2318 (May 1, 1995).

Levin et al., "Reversal of Chronic Ventricular Dilation in Patients With End–Stage Cardiomyopathy by Prolonged Mechanical Unloading", Circulation 91 (11): 2717–2720 (Jun. 1, 1995).

(List continued on next page.)

Primary Examiner—Carl Layno
(74) Attorney, Agent, or Firm—Merchant & Gould P.C.

(57) ABSTRACT

A device for treating cardiac disease of a heart includes a jacket of flexible material defining a volume between an open upper end and a lower end. The jacket is dimensioned for an apex of the heart to be inserted into the volume through the open upper end and for the jacket to be slipped over the heart. The jacket is adapted to be secured to the heart with the jacket having portions disposed on opposite sides of the heart. The jacket is adjustable to snugly conform to an external geometry of the heart and to constrain circumferential expansion of the heart during diastole and permit substantially unimpeded contraction of the heart during systole. A first and a second grid of electrodes are carried on the jacket. The grids are disposed to be in overlying relation to individual ones of the opposite sides of the heart when the jacket is secured to the heart. The first and second grids are connectable to a source of a defibrillating waveform.

11 Claims, 8 Drawing Sheets

U.S. PATENT DOCUMENTS

| | | | |
|---|---|---|---|
| 4,821,723 A | 4/1989 | Baker, Jr. et al. | 607/7 |
| 4,827,932 A | 5/1989 | Ideker et al. | 607/2 |
| 4,878,890 A | 11/1989 | Bilweis | 600/37 |
| 4,936,857 A | 6/1990 | Kulik | 623/3.1 |
| 4,957,477 A | 9/1990 | Lundback | 600/16 |
| 4,973,300 A | 11/1990 | Wright | 600/37 |
| 4,976,730 A | 12/1990 | Kwan-Gett | 623/3.26 |
| 5,057,117 A | 10/1991 | Atweh | 606/151 |
| 5,087,243 A | 2/1992 | Avitall | 604/20 |
| 5,131,905 A | 7/1992 | Grooters | 600/16 |
| 5,150,706 A | 9/1992 | Cox et al. | 607/105 |
| 5,186,711 A | 2/1993 | Epstein | 600/37 |
| 5,192,314 A | 3/1993 | Daskalakis | 623/3.21 |
| 5,256,132 A | 10/1993 | Snyders | 600/16 |
| 5,290,217 A | 3/1994 | Campos | 600/37 |
| 5,356,432 A | 10/1994 | Rutkow et al. | 623/23.72 |
| 5,383,840 A | 1/1995 | Heilman et al. | 600/17 |
| 5,385,156 A | 1/1995 | Oliva | 128/898 |
| 5,429,584 A | 7/1995 | Chiu | 600/18 |
| 5,507,779 A | 4/1996 | Altman | 607/5 |
| 5,524,633 A | 6/1996 | Heaven et al. | 600/562 |
| 5,603,337 A | 2/1997 | Jarvik | 128/898 |
| 5,647,380 A | 7/1997 | Campbell et al. | 128/898 |
| 5,702,343 A | * 12/1997 | Alferness | 600/37 |
| 5,713,954 A | 2/1998 | Rosenberg et al. | 600/17 |
| 5,800,334 A | 9/1998 | Wilk | 600/18 |
| 5,800,528 A | 9/1998 | Lederman et al. | 607/37 |
| 5,824,028 A | 10/1998 | Knisley | 607/119 |
| 5,928,278 A | * 7/1999 | Kitschmann | 607/129 |
| 6,076,013 A | * 6/2000 | Brennan et al. | 607/2 |
| 6,077,214 A | 6/2000 | Mortier et al. | 600/16 |
| 6,077,218 A | 6/2000 | Alferness | 600/37 |
| 6,085,754 A | * 7/2000 | Alferness et al. | 128/898 |
| 6,169,922 B1 | 1/2001 | Alferness et al. | 607/5 |

OTHER PUBLICATIONS

Oh et al., "The Effects of Prosthetic Cardiac Binding and Adynamic Cardiomyoplasty in a Model of Dilated Cardiomyopathy," J. Thorac. Cardiovasc. Surg., 116:148–153 (1998).

Revista Espanola de Cardiologia, vol. 51, No. 7 (Abstract in English)(Jul. 1998).

Vaynblat, M. et al., "Cardiac Binding in Experimental Heart Failure," Abstract in Supplement to Circulation 92(8):1810 (Oct. 15, 1995).

Vaynblat, M. et al., "Cardiac Binding in Experimental Heart Failure," Ann. Thorac. Surg., 64:81–85 (1997).

* cited by examiner

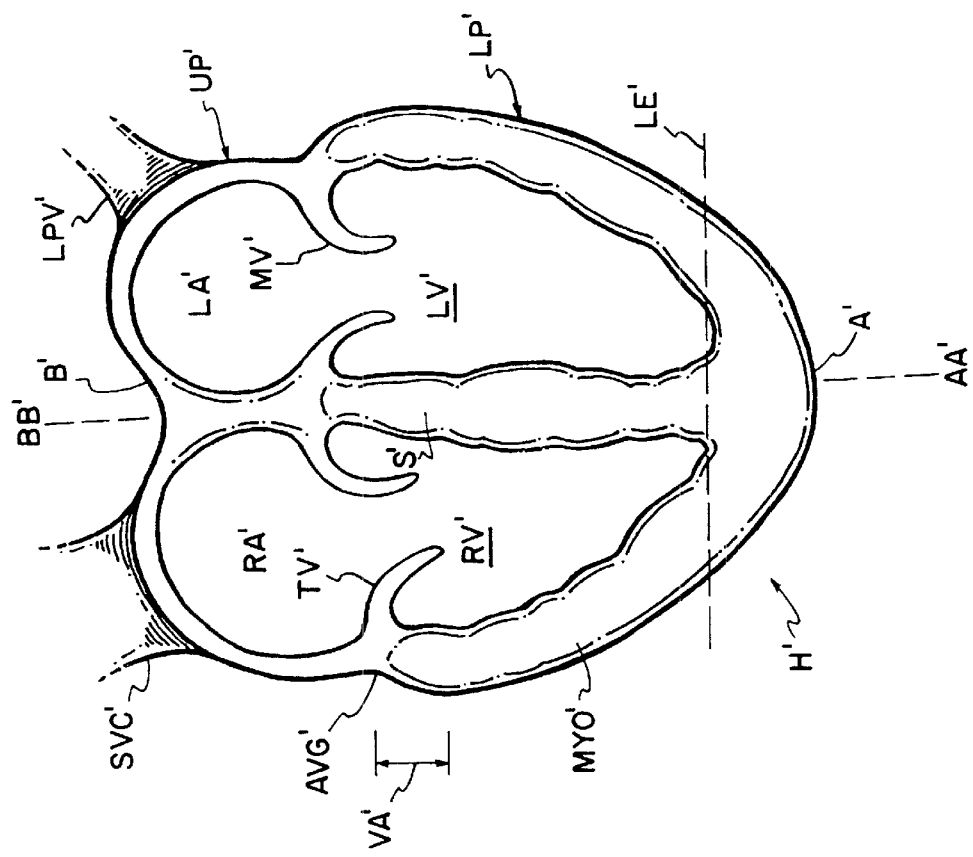
FIG. IA
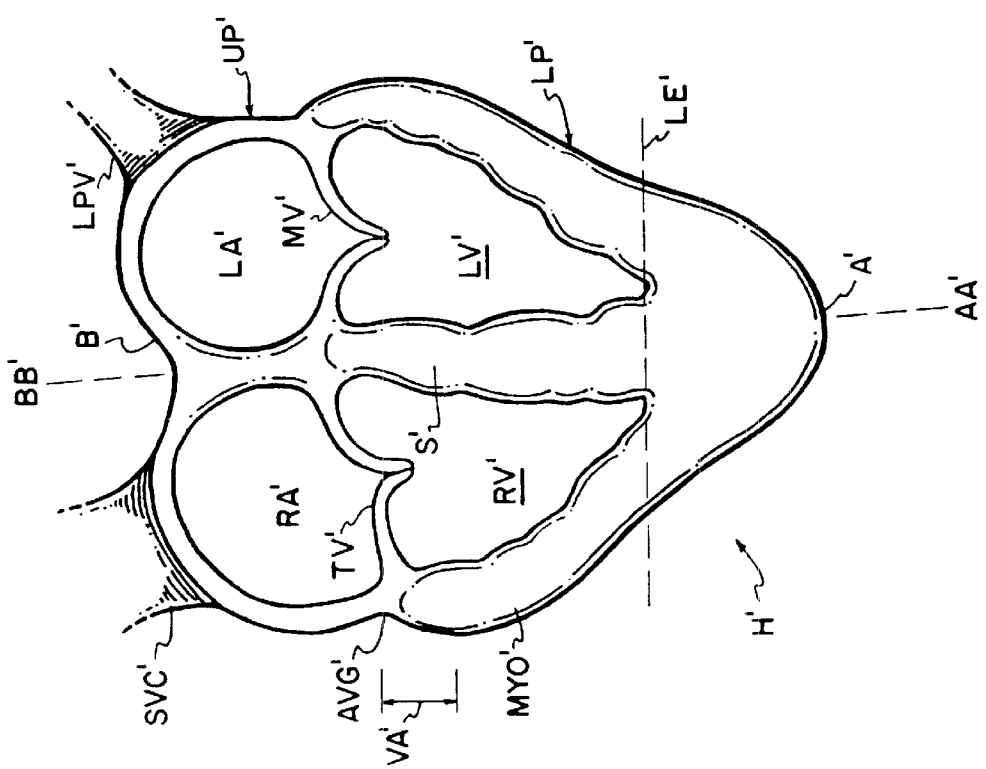
FIG. I

DEFIBRILLATING CARDIAC CONSTRAINT

This application is a continuation of application Ser. No. 09/628,706, filed Jul. 31, 2000, now U.S. Pat. No. 6,370,429, which is a continuation of Ser. No. 09/195,770, filed on Nov. 18, 1998, which issued as U.S. Pat. No. 6,169,922 on Jan. 2, 2001, which application(s) are incorporated herein by reference.

I. BACKGROUND OF THE INVENTION

1. Field of the Invention

The present invention pertains to a method for treating heart disease. More particularly, the present invention is directed to a method for treating congestive heart disease and related valvular dysfunction and to provide defibrillating treatments.

2. Description of the Prior Art

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the commonly prescribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1–2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist*, 91 *Circulation* 2314–2318 (1995). Similarly, cardiac binding is described in Oh et al., *The Effects of Prosthetic Cardiac Binding and Adynamic Cardiomyoplasty in a Model of Dilated Cardiomyopathy*, 116 *J. Thorac. Cardiovasc. Surg.* 148–153 (1998), Vaynblat et al., *Cardiac Binding in Experimental Heart Failure*, 64 *Ann. Thorac. Surg.* 81–85 (1997) and Capouya et al., *Girdling Effect of Nonstimulated Cardiomyoplasty on Left Ventricular Function*, 56 *Ann. Thorac. Surg.* 867–871 (1993).

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle into the aorta. Such surgeries are expensive. The devices are at risk of mechanical failure and frequently require external power supplies. TAH devices are used as temporary measures while a patient awaits a donor heart for transplant.

Commonly assigned U.S. Pat. No. 5,702,343 to Alferness dated Dec. 30, 1997 teaches a jacket to constrain cardiac expansion during diastole. Also, PCT International Publication No. WO 98/29401 published Jul. 9, 1998 teaches a cardiac constraint in the form of surfaces on opposite sides of the heart with the surfaces joined together by a cable through the heart or by an external constraint. U.S. Pat. No. 5,800,528 dated Sep. 1, 1998 teaches a passive girdle to surround a heart.

Patients suffering from congestive heart failure are frequently vulnerable to additional cardiac risks. For example, cardiac arrhythmias can arise. Defibrillation is a method to terminate fibrillation. As disclosed in commonly assigned and copending U.S. patent application Ser. No. 09/114,757 filed Jul. 13, 1998, a cardiac constraint device is preferably electrically permeable to permit application of an externally sourced defibrillating waveform. The prior art includes implantable defibrillators. An example of such an implantatable defibrillation is shown in European Patent Application No. 88301663.6 published Aug. 31, 1988 as Publication No. 0 280 564 A2. One object of the present invention to provide a cardiac constraint device which can also perform defibrillating functions.

II. SUMMARY OF THE INVENTION

According to a preferred embodiment of the present invention, a device is disclosed for treating cardiac disease of a heart. The device includes a jacket of flexible material defining a volume between an open upper end and a lower end of the jacket. The jacket is dimensioned for an apex of the heart to be inserted into the volume through the open upper end and for the jacket to be slipped over the heart. The jacket has a longitudinal dimension between the upper and lower ends sufficient for the jacket to constrain the lower portion of the heart between a valvular annulus and ventricular lower extremities. The jacket is adapted to be secured to the heart with the jacket having portions disposed on opposite sides of the heart between the valvular annulus and the ventricular lower extremities. The jacket is adjustable to snugly conform to an external geometry of the heart and to constrain circumferential expansion of the heart during diastole and permit substantially unimpeded contraction of the heart during systole. In one embodiment, a first and a second grid electrode is carried on the jacket. The grids are disposed to be in overlying relation to opposite sides of the heart when the jacket is secured to the heart. The first and second grids are connectable to a source of a defibrillating waveform.

III BRIEF DESCRIPTION OF THE DRAWINGS

FIG. 1 is a schematic cross-sectional view of a normal, healthy human heart shown during systole;

FIG. 1A is the view of FIG. 1 showing the heart during diastole;

IV. DESCRIPTION OF THE PREFERRED EMBODIMENT

A. Congestive Heart Failure

Figure 2B:
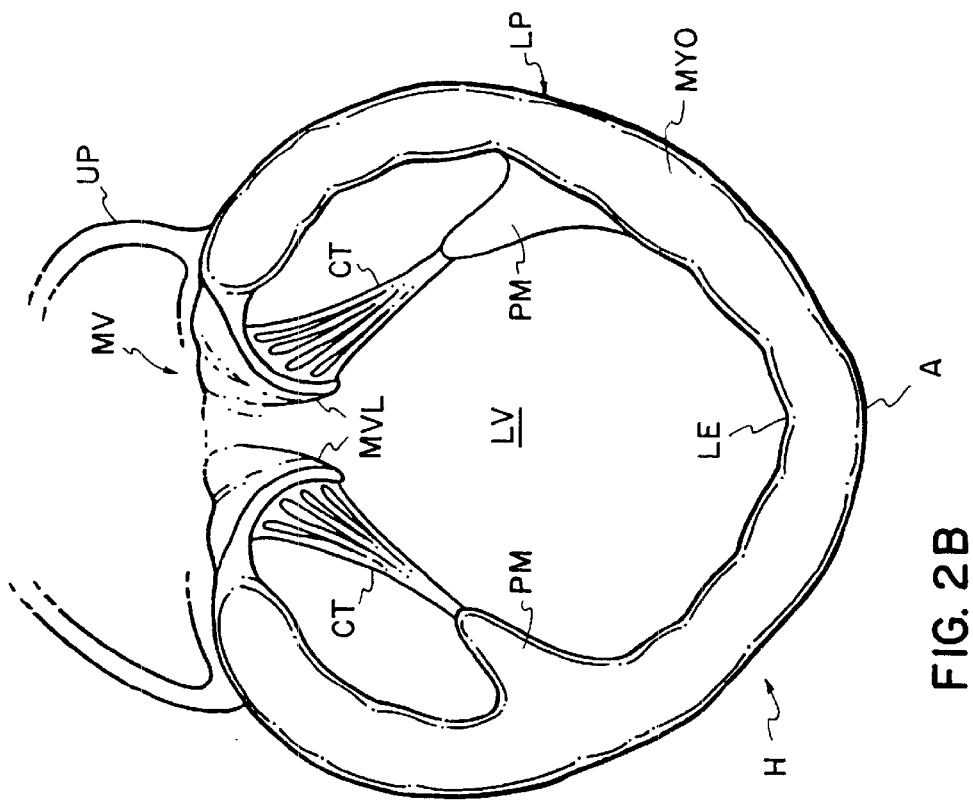
FIG. 2B is a view of FIG. 1B showing a diseased heart.

To facilitate a better understanding of the present invention, description will first be made of a cardiac constraint device such as is more fully described in commonly assigned and copending U.S. patent application Ser. No. 09/114,757 filed Jul. 13, 1998. In the drawings, similar elements are labeled similarly throughout.

Figure 1B:
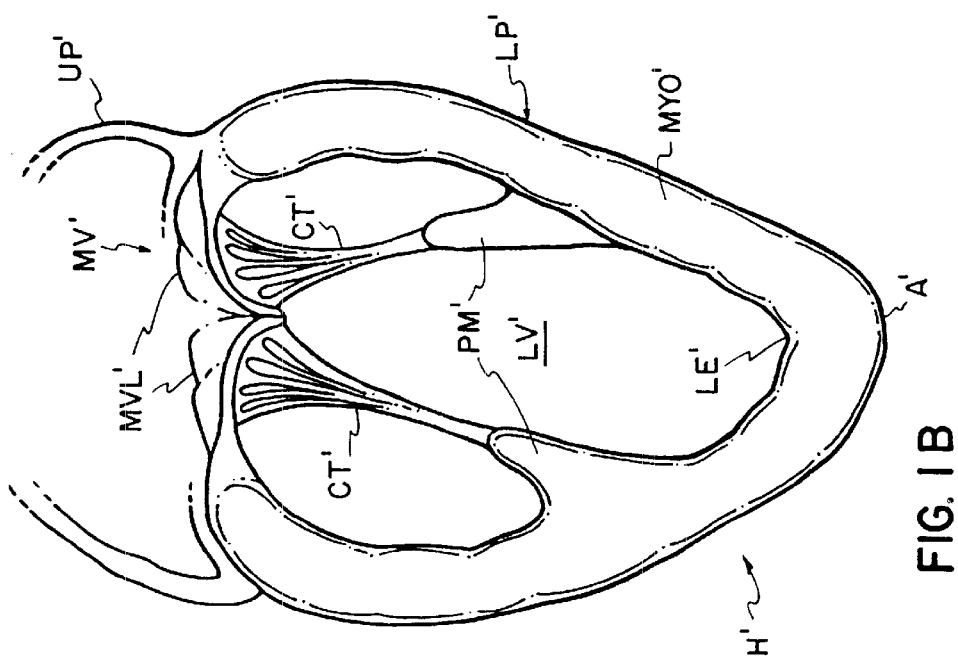
FIG. 1B is a view of a left ventricle of a healthy heart as viewed from a septum and showing a mitral valve.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis BB'-AA' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC', inferior vena cava IVC' and a left pulmonary vein LPV' are shown as being representative.

The heart H' contains valves to regulate blood flow between the chambers RA', RV', LA', LV' and between the chambers and the major vessels (e.g., the superior vena cava SVC', inferior vena cava IVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H'. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2A:
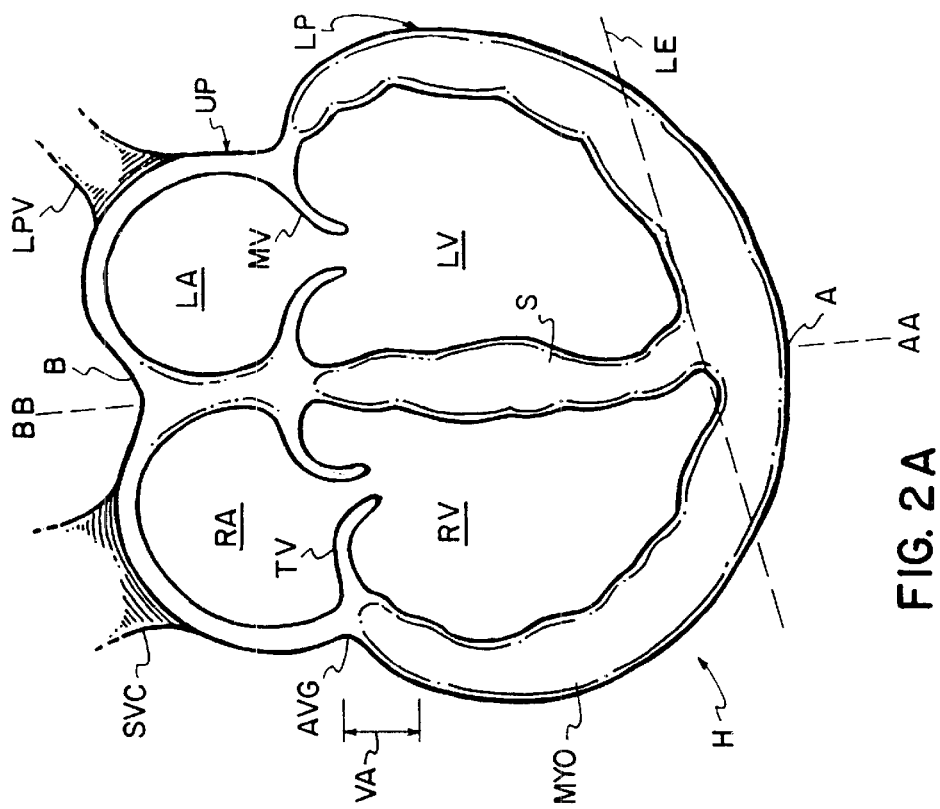
FIG. 2A is the view of FIG. 2 showing the heart during diastole.
Figure 2:
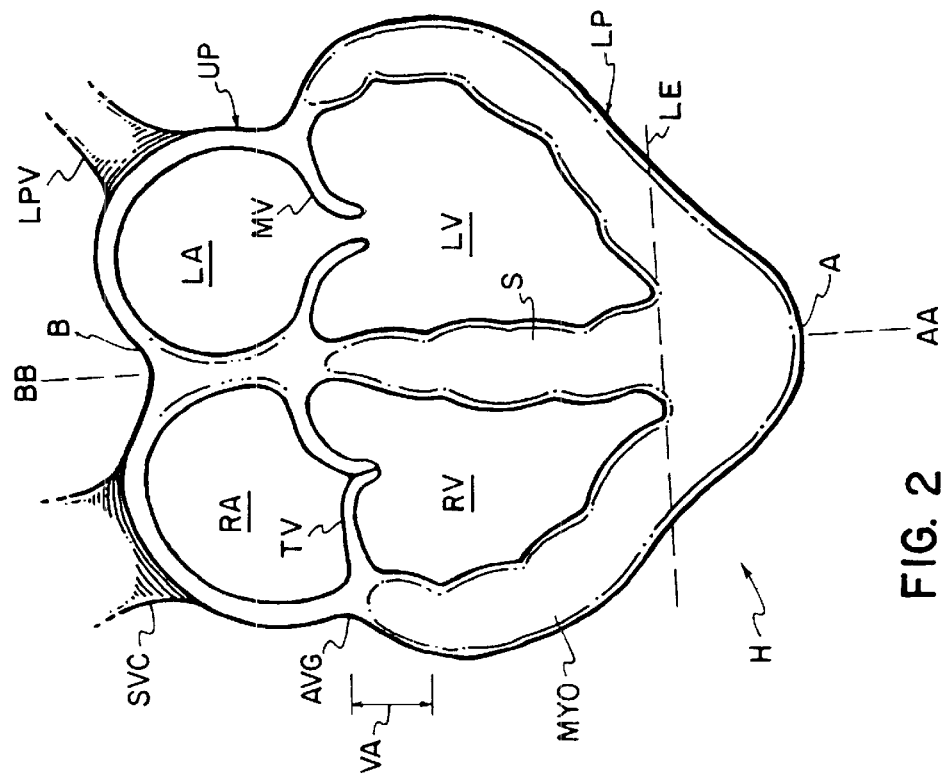
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

B. Cardiac Constraint Therapy

Having described the characteristics and problems of congestive heart disease, a treatment method and apparatus are described in commonly assigned and copending U.S. patent application Ser. No. 09/114,757 filed Jul. 13, 1998, now U.S. Pat. No. 6,085,754. In general, a jacket is configured to surround the myocardium MYO. While the method of the present invention will be described with reference to a jacket as described in commonly assigned and copending U.S. patent application Ser. No. 09/114,757 filed Jul. 13, 1998, it will be appreciated the present invention is applicable to any cardiac constraint device including those shown in U.S. Pat. No. 5,800,528 and PCT International Publication No. WO 98/29401.

Figure 3A:
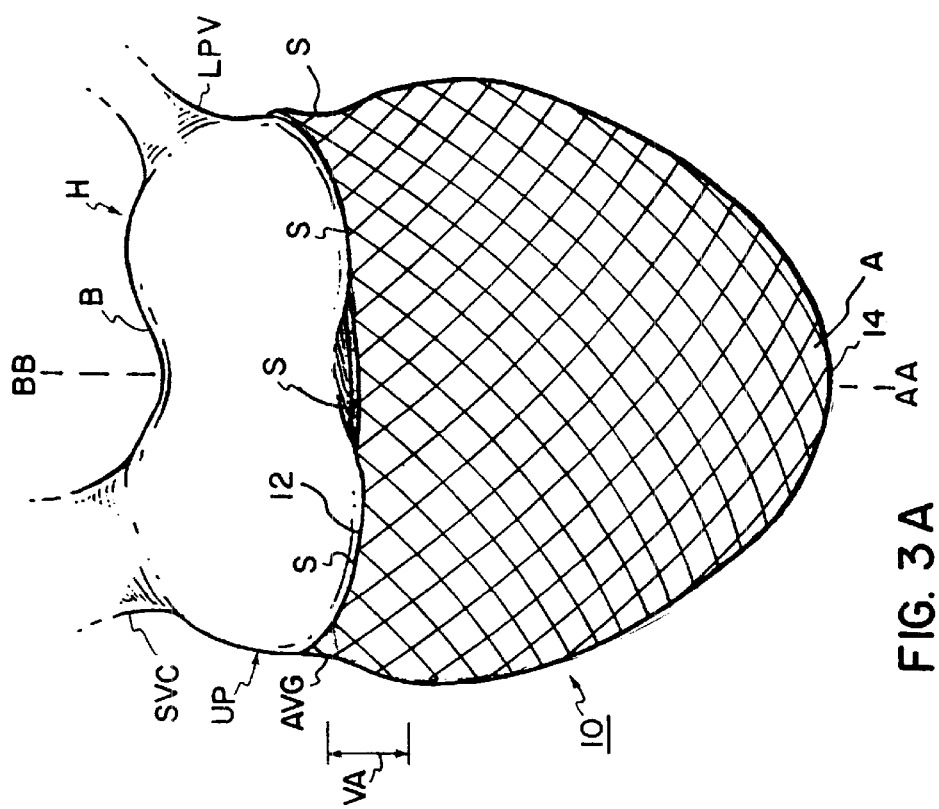
FIG. 3A is a side elevation view of a diseased heart in diastole with the device of FIG. 3 in place.
Figure 3:
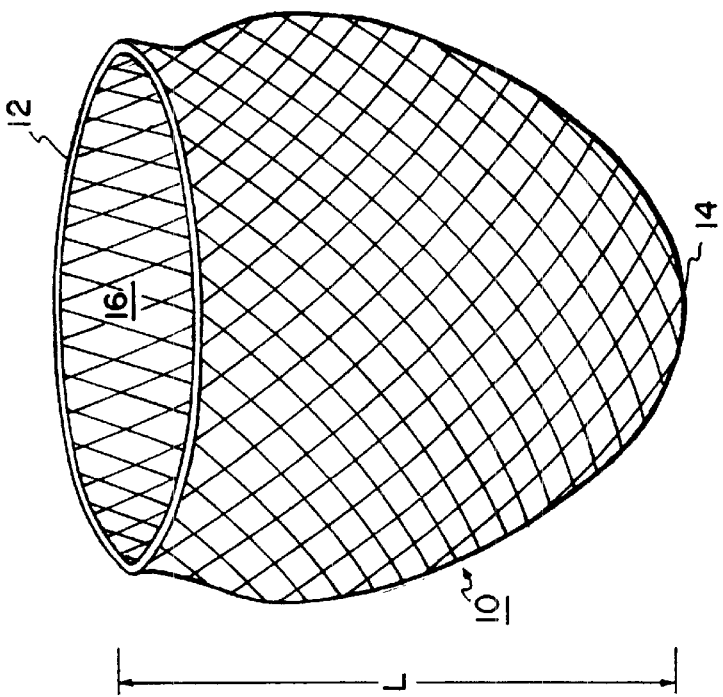
FIG. 3 is a perspective view of a cardiac constraint device to be used according to the method of the present invention.
Figure 4A:
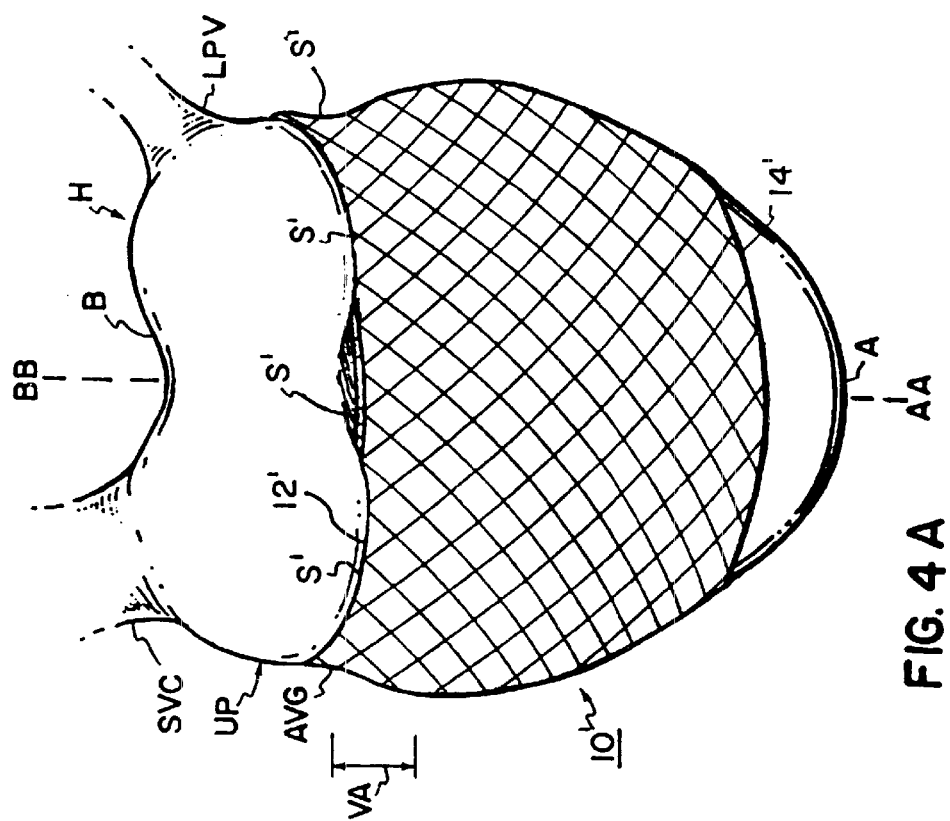
FIG. 4A is a side elevation view of a diseased heart in diastole with the device of FIG. 4 in place.
Figure 4:
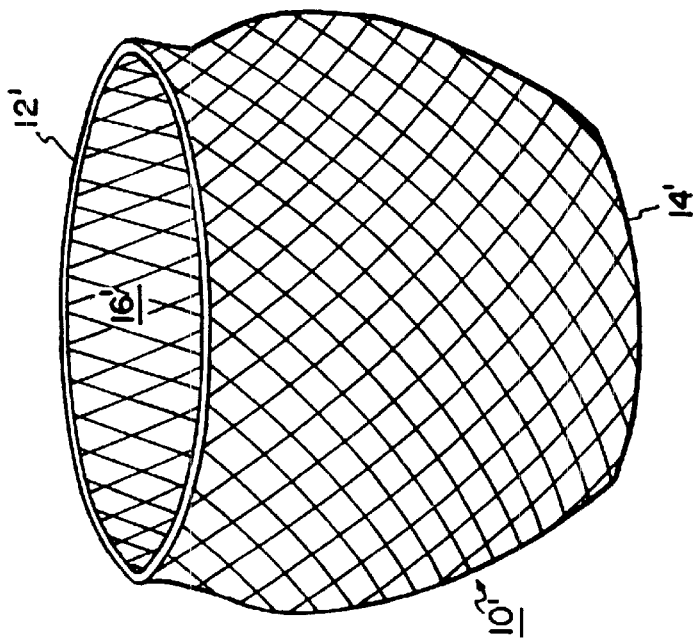
FIG. 4 is a perspective view of an alternative cardiac constraint device to be used according to the method of the present invention.

With reference now to FIGS. 3, 3A, 4 and 4A, the cardiac constraint device is shown as a jacket 10, 10' of flexible, biologically compatible material. The jacket 10 is an enclosed knit material having upper and lower ends 12, 12', 14, 14'. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to the valvular annulus VA and further extends to the lower portion LP to constrain at least the lower ventricular extremities LE.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10'. Such placement is desirable for the jacket 10, 10' to present a constraint against enlargement of the ventricular walls of the heart H.

After the jacket 10 is positioned on the heart H as described above, the jacket 10 is secured to the heart. Preferably, the jacket 10 is secured to the heart H through sutures. The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

Figure 5:
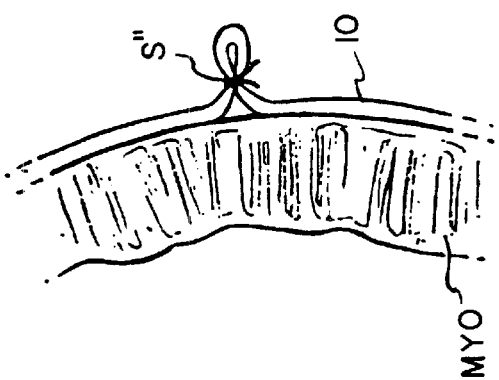
FIG. 5 is a cross-sectional view of the device of FIG. 3 overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 5) to reduce the volume of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 5, the jacket 10 can be provided with other arrangements for adjusting volume. For example, as disclosed in U.S. Pat. No. 5,702,343, the jacket can be provided with a slot. The edges of the slot can be drawn together to reduce the volume of the jacket.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

Figure 6:
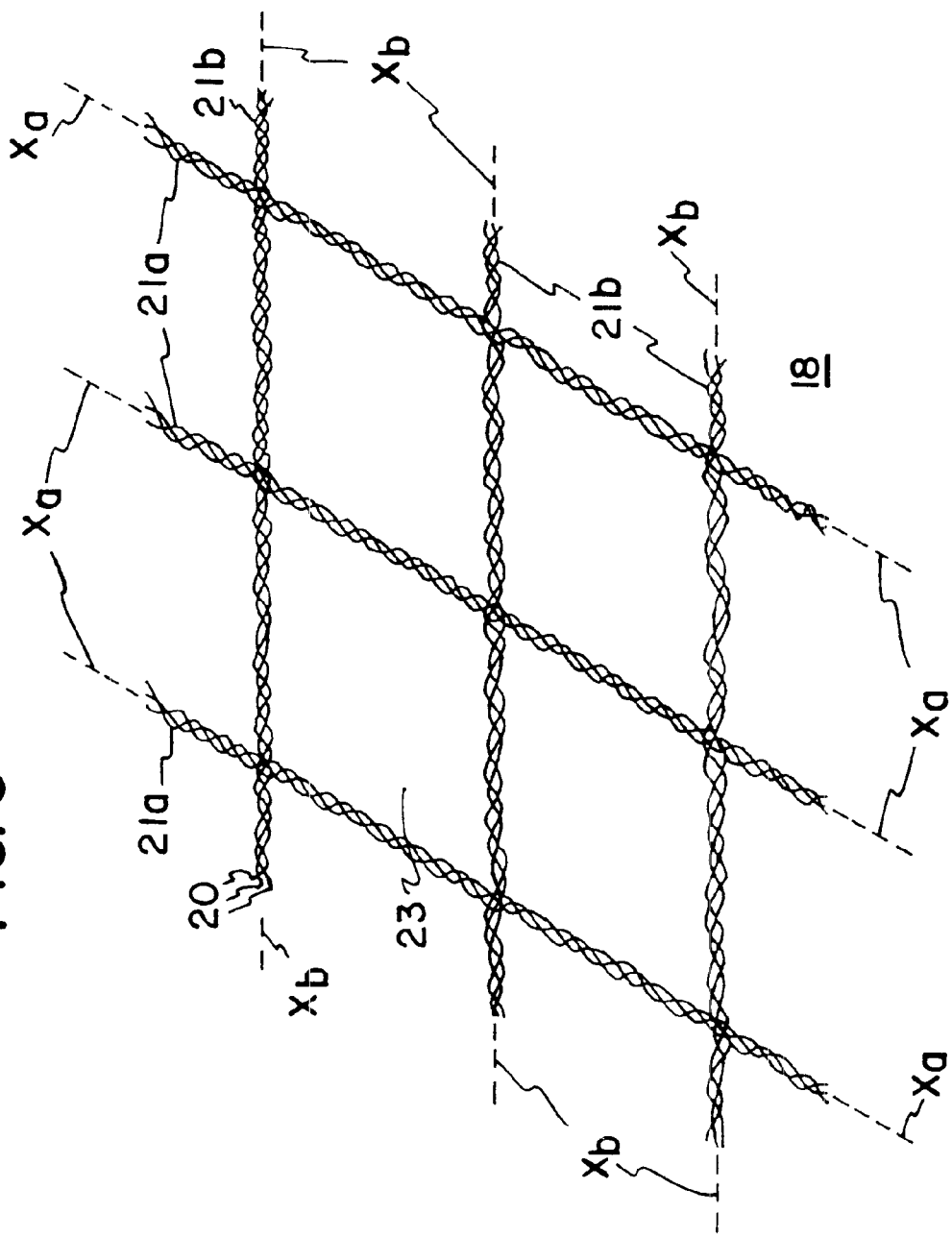
FIG. 6 is an enlarged view of a knit construction of the device of the present invention in a rest state.

As mentioned, the jacket 10 is constructed from a knit, biocompatible material. One embodiment of the knit 18 is illustrated in FIG. 6. Preferably, the knit is a so-called "Atlas knit" well known in the fabric industry. The Atlas knit is described in Paling, *Warp Knitting Technology*, p. 111, Columbine Press (Publishers) Ltd., Buxton, Great Britain (1970).

The Atlas knit is a knit of fibers 20 having directional expansion properties. More specifically, the knit 18, although formed of generally inelastic fibers 20, permits a construction of a flexible fabric at least slightly expandable beyond a rest state, FIG. 6 illustrates the knit 18 in a rest state. The fibers 20 of the fabric 18 are woven into two sets of fiber strands 21a, 21b having longitudinal axes $X_a$ and $X_b$. The strands 21a, 21b are interwoven to form the fabric 18 with strands 21a generally parallel and spaced-apart and with strands 21b generally parallel and spaced-apart.

Figure 7:
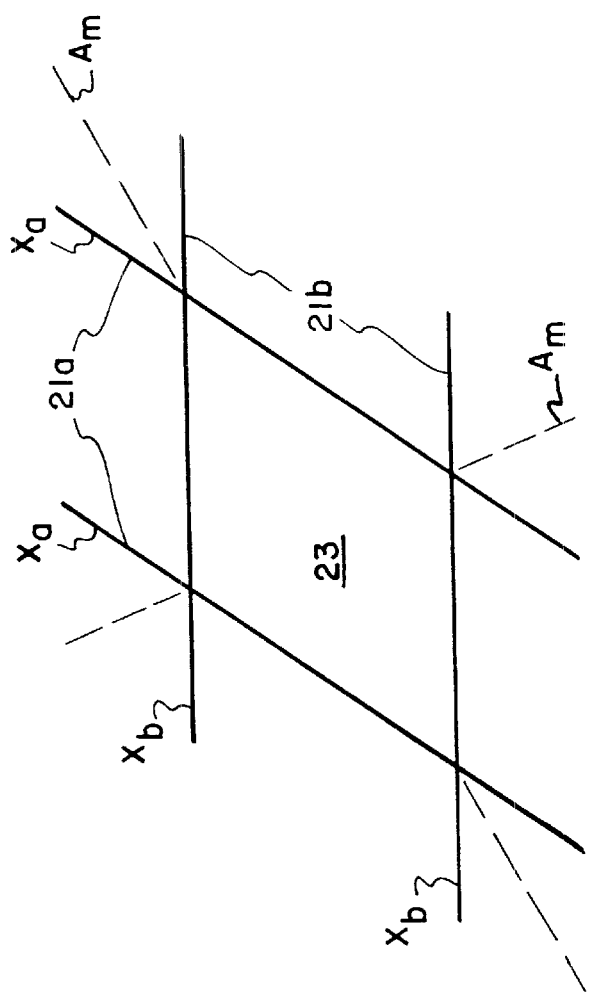
FIG. 7 is a schematic view of the material of FIG. 6.

For ease of illustration, fabric 18 is schematically shown in FIG. 7 with the axis of the strands 21a, 21b only being shown. The strands 21a, 21b are interwoven with the axes $X_a$ and $X_b$ defining a diamond-shaped open cell 23 having diagonal axes $A_m$. In a preferred embodiment, the axes $A_m$ are 5 mm in length when the fabric 18 is at rest and not stretched. The fabric 18 can stretch in response to a force. For any given force, the fabric 18 stretches most when the force is applied parallel to the diagonal axes $A_m$. The fabric 18 stretches least when the force is applied parallel to the strand axes $X_a$ and $X_b$. The jacket 10 is constructed for the material of the knit to be directionally aligned for a diagonal axis $A_m$ to be parallel to the heart's longitudinal axis AA-BB While the jacket 10 is expandable due to the above-described knit pattern, the fibers 20 of the knit 18 are preferably non-expandable. While all materials expand to at least a small amount, the fibers 20 are preferably formed of a material with a low modulus of elasticity. In response to the low pressures in the heart H during diastole, the fibers 20 are non-elastic. In a preferred embodiment, the fibers are 70 Denier polyester. While polyester is presently preferred, other suitable materials include polytetrafluoroethylene (PTFE), expanded PTFE (ePTFE) or polypropylene.

The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical conductivity between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

A large open area for cells 23 is desirable to minimize the amount of surface area of the heart H in contact with the material of the jacket 10 (thereby reducing fibrosis). However, if the cell area 23 is too large, localized aneurysm can form. Also, strand 21a, 21b can overly a coronary vessel with sufficient force to partially block the vessel. A smaller cell size increases the number of strands thereby decreasing the restricting force per strand. Preferably, a maximum cell area is no greater than about 6.45 $cm^2$ (about 2.54 cm by 2.54 cm) and, more preferably, is about 0.25 $cm^2$ (about 0.5 cm by 0.5 cm). The maximum cell area is the area of a cell 23 after the material of the jacket 10 is fully stretched and adjusted to the maximum adjusted volume on the heart H as previously described.

The fabric 18 is preferably tear and run resistant. In the event of a material defect or inadvertent tear, such a defect or tear is restricted from propagation by reason of the knit construction.

The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an antifibrosis lining (such as a PTFE coating on the fibers of the knit) could be placed between the heart H and the jacket 10. Alternatively, the fibers 20 can be coated with PTFE.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

C. Defibrillation Therapy

Figure 8:
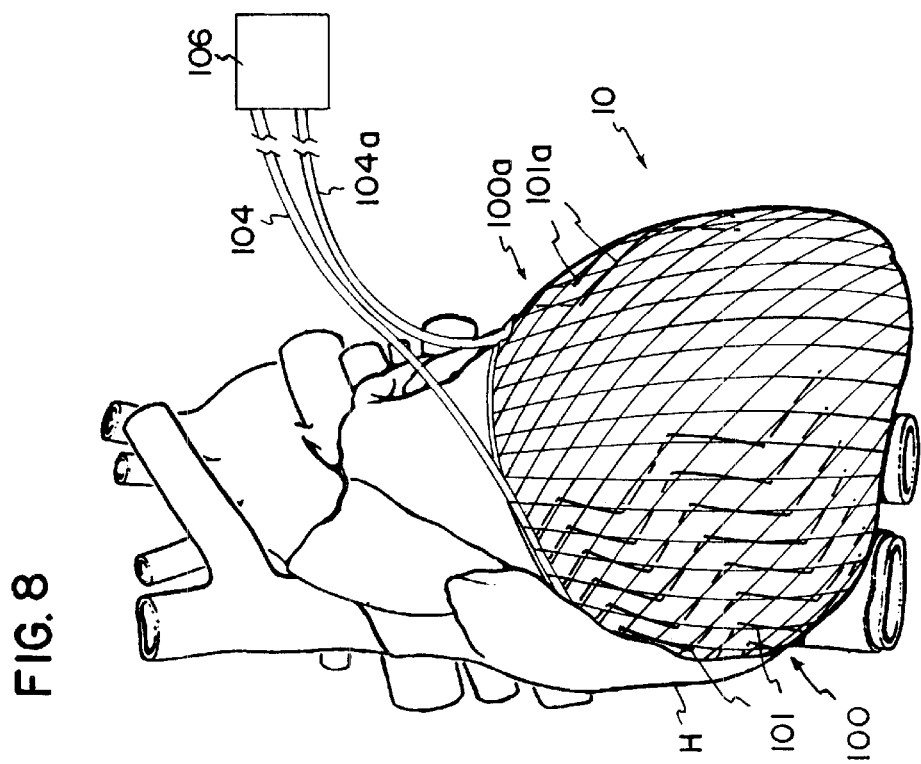
FIG. 8 is a view of the device of FIG. 3 secured to a heart and modified according to the teachings of the present invention.

FIG. 8 illustrates the device of FIG. 3 modified according to the present invention. In FIG. 8, an open cell jacket 10 of knit construction as previously described is placed on a heart H. The jacket 10 carries first and second electrode grids 100, 100a of electrode conductors 101, 101a. The conductors 101, 101a are bundled in insulated carriers 104, 104a. The carriers 104, 104a convey the conductors 101, 101a to an implantable source 106 of a defibrillating waveform.

Figure 9:
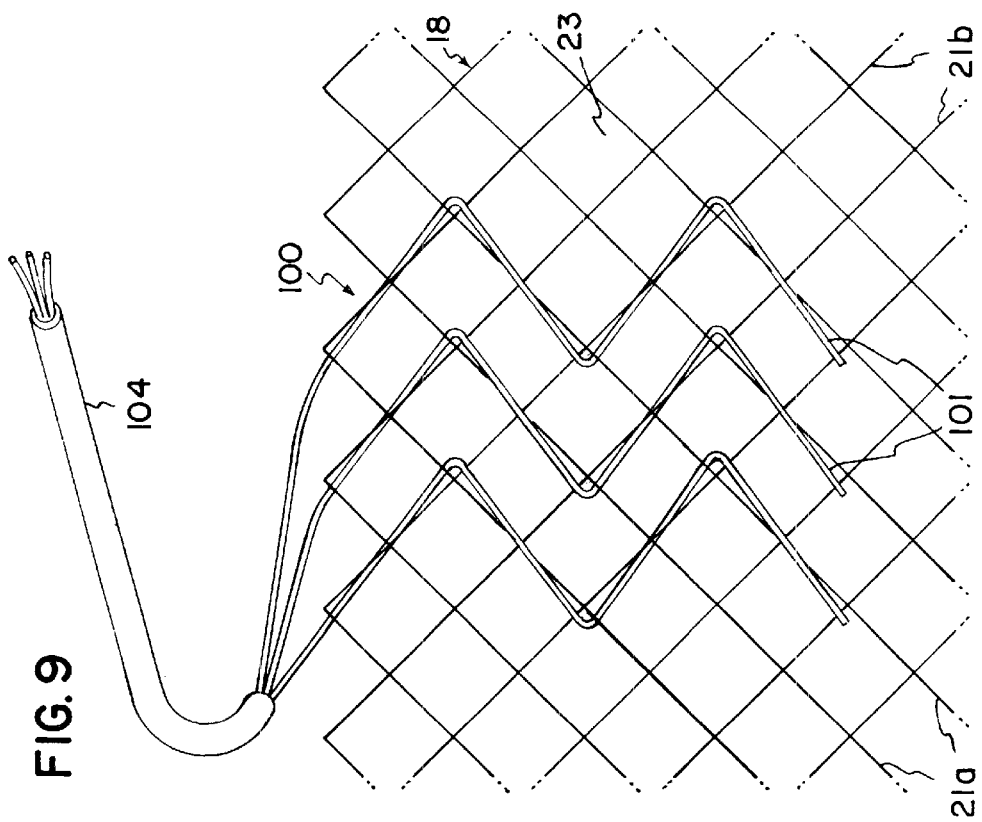
FIG. 9 is a view of the open cell material of the jacket of FIG. 8 and showing interwoven defibrillating conductors of an electrode grid.

FIG. 9 illustrates how the first grid 100 is incorporated into the material 18 of the jacket 10. Since second grid 100a is similarly incorporated, it is not separately shown and described in detail.

As previously described, the material 18 is a knit defining crisscrossing fiber strands 21a, 21b. The strands 21a, 21b define a grid of open cells 23. Uninsulated, electrically conductive electrode conductors 101 are interwoven through the cells 23. Examples of such electrode conductors 101 include titanium wire and platinum-coated stainless steel. Such electrode conductors 101 may be braided, multi-strand wires.

In one undulating pattern, the electrode conductors 101 are woven into alternating ones of the strands 21a, 21b. For example, an electrode conductor 101 may be woven into strand 21b for a distance equal to the length of two cells 23. Then, the electrode conductor 101 is woven into strand 21a for a distance equal to the length of two cells 23. This creates a zigzag pattern repeated along the length of the electrode conductor 101. For ease of illustration, FIG. 9 shows strands 21a, 21b as monofilament strands with conductors 101 positioned alongside the strands 21a, 21b. In fact, strands 21a, 21b are preferably multifilament as illustrated in FIG. 6 and the conductors 101 are interwoven into the multifilaments to securely position the conductors 101 on the jacket 10 and to maintain spacing between adjacent conductors 101.

The electrode conductors 101 extend in a direction parallel to the longitudinal axis of the heart. Opposing electrode conductors 101 are evenly spaced along their length.

The grids 100, 100a are positioned on the jacket 10 to overly opposite sides of the heart H after placement of the jacket 10 over the heart. Preferably, the grids 100, 100a overly the right and left lateral ventricular epicardium, respectively. As a result, a maximum amount of cardiac mass is located within the direct current path of a defibrillating shock.

As the jacket 10 is adjusted during placement, the cell size may very. Due to the jacket construction as described, the cell size around a circumference of the heart remains uniform. Therefore, during adjustment of the jacket, a uniform spacing between electrode conductors 101, 101a is retained.

With the construction as described, a defibrillating shock can readily be applied to a patient's heart treated with a cardiac constraint device. Further, the jacket 10 retains its electrical permeable quality permitting additional defibrillation applied external to the body. In defibrillators, the electrode conductors also act to receive signals from the heart. Since the electrode conductors are in close proximity to the heart, these electrode conductors permit easy detection of cardiac signals by the implantable defibrillator 106 facilitating analysis of electrical activity of the heart.

From the foregoing detailed description, the invention has been described in a preferred embodiment. Modifications and equivalents of the disclosed concepts are intended to be included within the scope of the appended claims. For example, the fibers 21a, 21b of the jacket material 18 may be selectively metalized with such fibers serving as the electrode conductors. Also, while the invention is shown overlying the ventricles, the jacket may overly the atria with grids over the atria to defibrillate the atria.

What is claimed is:

1. A device for treating a disease of a heart, the device comprising:

(a) a biocompatible material configured to engage a surface of the heart to relieve tension on a wall of the heart;

(b) one or more electrical elements operably connected to the biocompatible material and configured to contact a surface of the heart; and (c) the implantable source of an electrical impulse operably connected to the one or more electrical elements.

2. The device according to claim 1, wherein the device is configured to constrain cardiac expansion.

3. The device according to claim 2, wherein the device is adapted to be secured to the heart with portions disposed on opposites sides of the heart.

4. The device according to claim 2, wherein one or more electrical elements comprise an electrode grid.

5. The device according to claim 2, wherein the one or more electrical elements comprise at least a first and a second electrode grid.

6. The device according to claim 5, wherein the electrode grid comprises a plurality of electrode conductors intertwined with strands of the jacket material.

7. The device according to claim 5, wherein the electrode grid is configured to overly a surface of the heart.

8. The device according to claim 5, wherein the electrode grid is configured to maintain spacing between adjacent electrode conductors.

9. The device according to claim 5, wherein the electrode grid comprises titanium or platinum coated stainless steel.

10. The device according to claim 2, wherein the electrical elements are capable of receiving signals from the heart.

11. The device according to claim 2, wherein the electrical elements comprise defibrillating electrodes.

* * * * *

UNITED STATES PATENT AND TRADEMARK OFFICE
CERTIFICATE OF CORRECTION

PATENT NO. : 6,567,699 B2
DATED : May 20, 2003
INVENTOR(S) : Alferness et al.

It is certified that error appears in the above-identified patent and that said Letters Patent is hereby corrected as shown below:

Column 3,
Lines 41-42, "implantatable" should read -- implantable --

Column 8,
Line 58, "Also, strand" should read -- Also, a strand --

Column 9,
Lines 47-48, "21 a" should read -- 21a --

Column 10,
Line 45, "opposites" should read -- opposite --

Signed and Sealed this

Second Day of September, 2003

JAMES E. ROGAN
*Director of the United States Patent and Trademark Office*